US00PP21793P2

(12) United States Plant Patent
Kraan

(10) Patent No.: US PP21,793 P2
(45) Date of Patent: Mar. 22, 2011

(54) *WEIGELA* PLANT NAMED 'BOKRAFOUR'

(50) Latin Name: *Weigela florida*
Varietal Denomination: Bokrafour

(76) Inventor: Kees Jan Kraan, Papenveer (NL)

( * ) Notice: Subject to any disclaimer, the term of this patent is extended or adjusted under 35 U.S.C. 154(b) by 5 days.

(21) Appl. No.: 12/589,422

(22) Filed: Oct. 23, 2009

(51) Int. Cl.
*A01H 5/00* (2006.01)

(52) U.S. Cl. ..... Plt./226
(58) Field of Classification Search ..... Plt./226
See application file for complete search history.

*Primary Examiner*—June Hwu
*Assistant Examiner*—Louanne C Krawczewicz Myers
(74) *Attorney, Agent, or Firm*—Penny J. Aguirre

(57) ABSTRACT

A new cultivar of *Weigela florida*, 'Bokrafour', characterized by its green foliage, its compact plant habit, and its abundantly produced red-purple flowers.

2 Drawing Sheets

Botanical classification: *Weigela florida.*
Variety denomination: 'Bokrafour'.

BACKGROUND OF THE INVENTION

The present invention relates to a new and distinct cultivar of *Weigela florida* and will be referred to hereafter by its cultivar name, 'Bokrafour'. 'Bokrafour' is a new cultivar of old fashion *weigela*, a shrub grown for use as an ornamental landscape plant.

The new cultivar of *Weigela* is a selection from an ongoing breeding program conducted by the Inventor in Boskoop, The Netherlands with the objective of creating new cultivars of *Weigela* with compact plant habits and attractive foliage coloration.

The new variety of *Weigela*, 'Bokrafour', designated as accession no. 00090-04 was selected from seedlings derived from open pollination of an unnamed proprietary seedling of *Weigela florida* in summer of 2000. The female parent, designated as accession no. 93115, derived from open pollination of the cultivar 'Evita' (not patented). The male parent of 'Bokrafour' is unknown. After 6 years of observation, 'Bokrafour' was selected as a single unique plant in summer of 2007.

Asexual reproduction of the new cultivar was first accomplished by the Inventor using softwood stem cuttings in summer of 2007 in Boskoop, The Netherlands. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial plot for eight years in Boskoop, The Netherlands. These attributes in combination distinguish 'Bokrafour' as a unique cultivar of *Weigela.*

1. 'Bokrafour' exhibits a compact plant habit.
2. 'Bokrafour' exhibits green foliage.
3. 'Bokrafour' is very floriferous and exhibits an abundance of red-purple flowers.

In comparison to 'Evita', one of the parents in the breeding background of 'Bokrafour', 'Bokrafour' has flowers that are red-purple in color whereas 'Evita' has flowers that are red in color. 'Bokrafour' can be most closely compared to the cultivars 'Victoria' and 'Minuet' (both unpatented). 'Victoria' differs from 'Bokrafour' in being taller in plant height, in having a much less compact plant habit, and in having dark brown-green foliage. 'Minuet' is similar to 'Bokrafour' in having a compact plant habit, but differs from 'Bokrafour' in being lower growing, in being less floriferous, and in having bronze-green to brownish green foliage.

BRIEF DESCRIPTION OF THE DRAWING

The accompanying colored photographs were taken in May and illustrate the overall appearance and distinct characteristics of 8 year-old plants the new *Weigela* as grown in a trial plot in Boskoop, The Netherlands.

The photograph in FIG. 1 provides an overall view of the growth habit and blooming habit of 'Bokrafour'.

Figure 1:
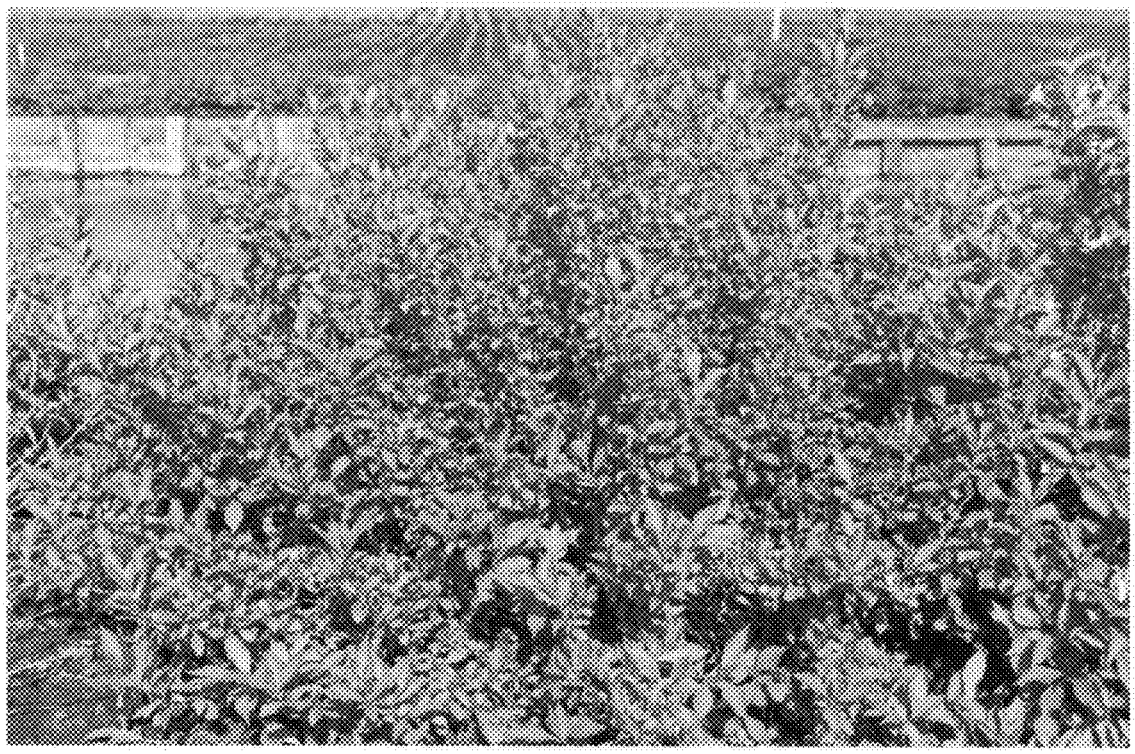
Figure 2:
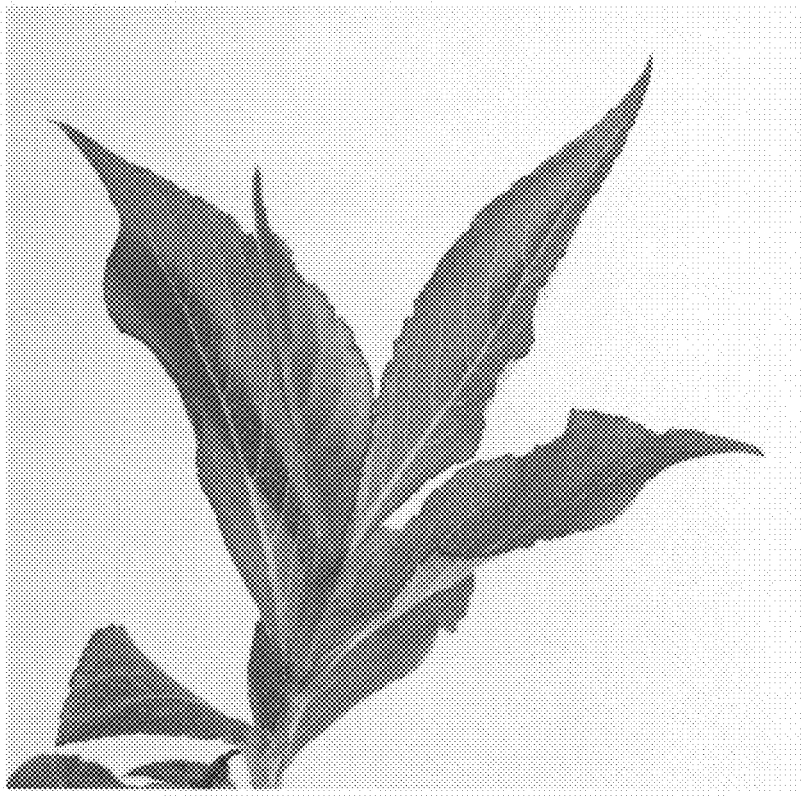

The photograph in FIG. 2 provides a close-up view of the foliage of 'Bokrafour'.

Figure 3:
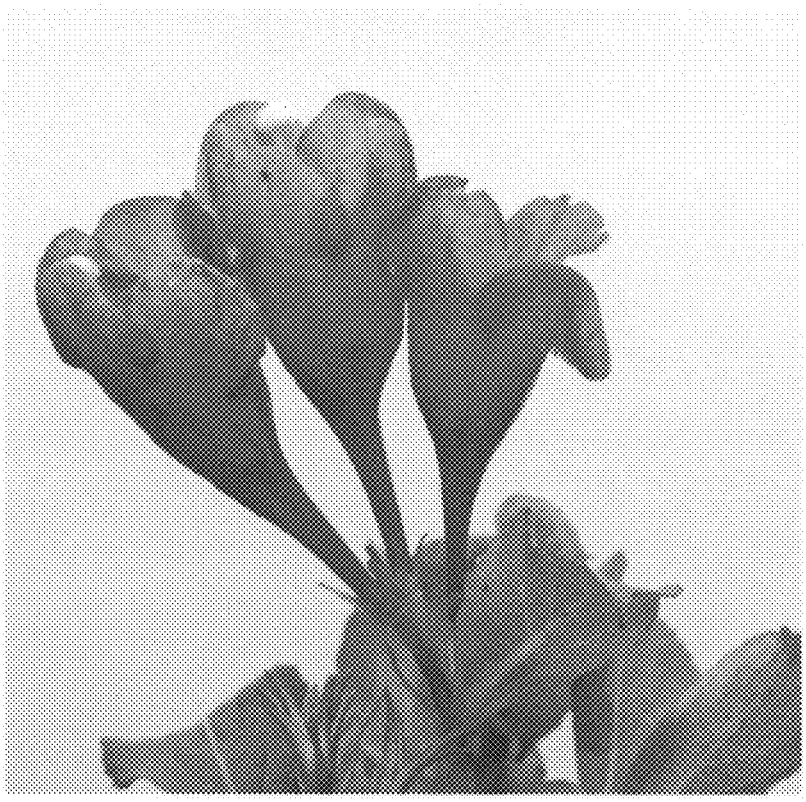

The photograph in FIG. 3 provides a close-up view of the flowers of 'Bokrafour'.

The colors in the photograph may differ slightly from the color values cited in the detailed botanical description, which accurately describe the colors of the new *Weigela.*

DETAILED BOTANICAL DESCRIPTION

The following is a detailed description of 8 year-old plants of the new cultivar as grown outdoors in full sun in a trial plot in Boskoop, The Netherlands. Plants were grown under average day temperatures of 15° C. to 28° C. and average night temperature of 7° C. to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms profusely for about 4 weeks in May in Boskoop, The Netherlands.

*Plant type.*—Deciduous shrub.

*Plant habit.*—Compact, broadly upright.

*Plant size.*—Reaches about 80 cm in height and 117 cm in width.

*Hardiness.*—At least in U.S.D.A. Zones 5 to 9.

*Environmental stress.*—Highly tolerant to wind and rain.

*Diseases and pests.*—No susceptibility or resistance to diseases or pests has been observed, similar to other *Weigela* known to the Inventor.

*Root description.*—Fibrous, moderately dense.

Growth and propagation:

*Propagation.*—Softwood stem cuttings.

*Root initiation.*—An average of 30 days at soil temperatures of 20° C.

*Root development.*—An average of 26 weeks at air temperatures of 18° C. to finish a young plant.

*Growth rate.*—Moderate, about 8 cm per month in spring.

Stem description:

*Shape.*—Slightly quadrangular with older branches rounded.

*Stem color.*—New growth; 152C tinged with 176A and 176B, mature wood; 199B and 199C.

*Stem size.*—An average of 45.7 cm in length and 3.5 mm in diameter.

*Stem surface.*—New growth; moderately glossy with more terminal portion of stems pubescent with hairs about 0.5 mm in length and 155B in color, mature wood is dull and glabrous.

*Stem aspect.*—Upright to outward at an angle of 45°.

*Branching.*—Basal branching, an average of 134 lateral branches.

Foliage description:

*Leaf shape.*—Elliptic.

*Leaf division.*—Simple.

*Leaf base.*—Short attenuate.

*Leaf apex.*—Acuminate.

*Leaf fragrance.*—None.

*Leaf venation.*—Pinnate, 153D in color on upper surface, N170D in color on lower surface.

*Leaf margins.*—Finely serrate, pubescent with hairs about 0.5 mm in length and 158A and 158B in color.

*Leaf arrangement.*—Opposite.

*Leaf attachment.*—Petiolate.

*Leaf surface.*—Upper surface; moderately glossy with main vein moderately covered with hairs about 0.5 mm in length and 158A and 158B in color, lower surface; moderately glossy with main vein and secondary veins moderately covered with hairs about 0.5 mm in length and 158A and 158B in color.

*Leaf internode length.*—An average of 3.2 cm.

*Leaf size.*—An average of 4.7 cm in length and 2.2 cm in width.

*Leaf quantity.*—An average of 28 per stem.

*Leaf color.*—New growth; upper surface 143A and 144A, lower surface 146C, mature growth; upper surface 146A and 146B, lower surface 147B and 147C.

*Petioles.*—About 5 mm in length and 1.5 mm in width, 151A in color and tinged with 175C.

*Stipules.*—None.

Inflorescence description:

*Inflorescence type.*—Solitary, in pairs, or in small clusters at terminus and leaf axils.

*Inflorescence size.*—From 3.9 cm in depth and 1.8 cm in diameter when a solitary flower and up to 4 cm in depth and 12 cm in diameter when in clusters.

*Flower buds.*—Narrowly obovate in shape, an average of 2.9 cm in depth and 8 mm in diameter, 61A and 61C in color.

*Flower fragrance.*—None.

*Lastingness of flowers.*—About 12 days with about 90% of flowers in bloom at one stage, self-cleaning.

*Flower aspect.*—Outward to upright.

*Flower quantity.*—An average of 96 per stem, an average of 10,000 per plant 8 years in age.

*Flower type.*—Tubular.

*Flower size.*—Average of 1.8 cm in diameter and 3.9 cm in depth.

*Peduncles.*—Average of 1.1 cm in length and 1 mm in diameter, 152B in color, glabrous surface, oval in shape.

*Pedicels.*—None, sessile to peduncle.

*Calyx.*—Rotate in shape, an average of 8 mm in depth and 4 mm in width.

*Sepals.*—5, linear in shape, narrowly acute apex, narrowly cuneate base, entire margin, an average of 8 mm in length and 1 mm in width, 146C in color on upper surface and 146C and heavily tinged with 185A on lower surface, surface is glabrous on both surfaces.

*Petals.*—5, lower 75% fused into tube, spathulate in shape, margin entire on free portion, apex obtuse, an average of 3.9 cm in length with free portion an average of 1 cm in width, outer and inner surface is smooth and glabrous, color of inner surface when opening and mature; 63B blending with 70B with tube 60A and 60B, color of outer surface when opening and mature; 63B with tube 60A, color of both surfaces fade to 70C.

Reproductive organs:

*Gynoecium.*—1 pistil, about 3.9 cm in length, style is an average of 3.7 cm in length, and 157D in color and tinged at base with 142D, stigma is club-shaped and 157D in color, ovary is 152B in color.

*Androcoecium.*—5 stamens, filaments are 63B in color and an average of 1.5 cm in length, anthers are 162C in color, an average of 4 mm in length, basifixed and narrowly oblong in shape, pollen is low in quantity and 158D in color.

*Fruit and seed.*—No fruit or seed production has been observed to date.

It is claimed:

1. A new and distinct cultivar of *Weigela* plant named 'Bokrafour' as herein illustrated and described.

* * * * *